United States Patent [19]

Conte et al.

[11] Patent Number: 5,476,654
[45] Date of Patent: Dec. 19, 1995

[54] PROCESS FOR PREPARING PHARMACEUTICAL COMPOSITIONS HAVING AN INCREASED ACTIVE SUBSTANCE DISSOLUTION RATE, AND THE COMPOSITIONS OBTAINED

[75] Inventors: Ubaldo Conte, Busto Arsizio; Aldo La Manna; Paolo Giunchedi, both of Pavia, all of Italy

[73] Assignee: Jagotec AG, Italy

[21] Appl. No.: 321,123

[22] Filed: Oct. 11, 1994

Related U.S. Application Data

[63] Continuation of Ser. No. 76,477, Jun. 14, 1993, abandoned, which is a continuation of Ser. No. 733,457, Jul. 22, 1991, abandoned.

[30] Foreign Application Priority Data

Jul. 27, 1990 [IT] Italy .................................. 21091A/90

[51] Int. Cl.$^6$ ........................................ A61K 9/20
[52] U.S. Cl. ...................... 424/78.08; 424/464; 424/465; 424/468; 424/470
[58] Field of Search ..................... 426/464, 465, 426/468, 470, 499; 514/960, 964, 777, 781; 424/78.08

[56] References Cited

U.S. PATENT DOCUMENTS

| | | | |
|---|---|---|---|
| 3,966,899 | 6/1976 | Nakai et al. .................... | 424/468 |
| 4,343,789 | 8/1982 | Kawata et al. .................... | 514/356 |
| 4,439,453 | 3/1984 | Vogel .................................... | 514/629 |
| 4,639,370 | 1/1987 | Carli .................................... | 514/772.5 |
| 4,886,669 | 12/1989 | Ventrouras ........................ | 424/469 |
| 4,937,079 | 6/1990 | Farolfi et al. .................... | 424/485 |
| 5,082,669 | 1/1992 | Shirai et al. ........................ | 424/495 |
| 5,085,869 | 2/1992 | Olthoff et al. .................... | 424/499 |
| 5,225,192 | 7/1993 | Lourecich ........................ | 424/78.01 |

FOREIGN PATENT DOCUMENTS 0371431  6/1990  European Pat. Off. .

OTHER PUBLICATIONS

Seiyaku et al., Chemical Abstracts, 101 (12), Abstract 97637 (Sep. 1984).

Kawano et al, Biological Abstracts 82(3) Abstract 27082 (1986).

*Primary Examiner*—John C. Bleutge
*Assistant Examiner*—Robert H. Harrison

[57] ABSTRACT

A process is described for preparing pharmaceutical compositions by co-grinding or dry mixing the active substance with cyclodextrins or with hydrophilic polymer materials which swell on contact with water. Homogeneous compositions are obtained from which the active substance is released very rapidly into an aqueous medium.

4 Claims, No Drawings

PROCESS FOR PREPARING PHARMACEUTICAL COMPOSITIONS HAVING AN INCREASED ACTIVE SUBSTANCE DISSOLUTION RATE, AND THE COMPOSITIONS OBTAINED

This is a continuation of application Ser. No. 076,477, filed Jun. 14, 1993, now abandoned, which is a continuation of application Ser. No. 733,457, filed Jul. 22, 1991, now abandoned.

PRIOR ART

The problem of increasing the dissolution rate of active substances which are poorly soluble in water is felt in many fields ranging from phytopharmaceuticals to pesticides and in general in all those fields in which bioactive substances are used, but it is the pharmaceutical field which is most concerned with the availability of substances of high water solubility, this being an essential characteristic for obtaining high bioavailability of the active substance.

This requirement is particularly felt in the case of substances which when administered orally must undergo dissolution prior to their passage through biological membranes.

In addition, in the case of solid pharmaceutical forms for oral administration, the release of the active substance is the most important step in determining therapeutic activity.

The release of a therapeutically active substance from a solid pharmaceutical form can be represented by the following scheme:

```
                              Medicament in solid
                              particle form
┌──────────────────┐              ■ ■ ■ ■ ■ ■
│ Medicament in its│ Disgregation                  Dissolution
│pharmaceutical form│─────────→   ■ ■ ■ ■ ■ ■   ─────────→
└──────────────────┘

┌──────────────┐   Absorption          ┌──────────────┐
│ Medicament in│ ─────────→            │ Medicament in│
│   solution   │                       │  the body    │
└──────────────┘                       └──────────────┘
```

In the case of pharmaceutical tablets the rate of the first step (disgregation of the pharmaceutical form) can be increased by a proper choice of formulation constituents, whereas the kinetics of the next step (dissolution of the active principle, normally indicated as the dissolution rate) is determined by the physicochemical characteristics of the active substance and in particular by its solubility in water.

The dissolution Pate of the active principle is therefore the limiting factor in the absorption process and its therapeutic activity.

The dissolution of an active substance is also known to be controlled by the Noyes and Withney equation, which can be expressed in the following form:

$$\frac{dc}{dt} = \frac{D}{h} S (C_S - C)$$

where:

$dc/dt$ = dissolution rate, i.e. the quantity of substance which dissolves in unit time $D$ = substance diffusion coefficient (which depends on the M. W. the viscosity of the medium, temperature etc.)

$h$ = thickness of diffusion layer $S$ = total surface area exposed to the diffusion fluid $C_S$ = concentration of substance in the diffusion layer $C$ = concentration of medicament in the undiluted solution.

Many attempts have made to modify the parameters which influence dissolution rate. Micronized active substances are particularly widely used, to obtain products with a large surface area.

This expedient has been used to increase the dissolution rate of chloramphenicol palmitate, nitrofurantoin and griseofulvin, even though particularly in this latter case there is a corresponding marked increase in product toxicity.

It has also been found in the case of nifedipine that a rapid medicament effect can be obtained using the micronized product, whereas a slower effect can be obtained by using the active principle at a coarser particle size. This process, which is not easy to standardize, is claimed in German patents 2209526 and DE A1 033919.

The problem of increasing the dissolution rate of poorly soluble active substances has been confronted in various other ways, for example by transforming the substance from a crystalline state to an amorphous state which generally results in an increase in dissolution rate [see Gouda M. W. and coil., Drug Develop. Ind. Pharm. 3,273 (1977)].

Attempts have been made to attain the same objective by preparing clathrates, inclusion compounds, complexes with polymers such as polyvinylpyrrolidone, polyethyleneglycol, polyvinylalcohol, cellulose and derivatives or, more recently, cyclodextrins.

A more recent method for obtaining an increased dissolution rate is described by Nakay Y and coil. Chem. Pharm. Bull. 25, 3340 (1977), in which the poorly soluble active principle is absorbed onto an inert support having a large surface area.

A different process, claimed in Italian patent application 20474 A/85, comprises solubilizing the poorly water-soluble active principle in an organic solvent (generally apolar) and then loading the obtained solution onto a support of hydrophilic polymer material able to swell on contact with water and aqueous fluids.

However this method requires the use of a very complicated process in that generally the supporting polymer material must be uniformly coated and brought into intimate contact with the organic solution of the active substance.

This means that large quantities of solvent must generally be treated to obtain solutions able to be uniformly distributed on the supporting polymer material.

This process also requires the use of large solvent volumes with considerable drawbacks both from the technical viewpoint (possible flammability or ease of explosion) and economic viewpoint (high cost and need to use explosion-proof plant).

It is also essential to use suitable technical processes able to completely eliminate the apolar solvent from the support, to avoid the risk of any residual solvent presence.

This is obviously of extreme importance in the case of biologically active substances and medicaments for human use, and is evaluated with extreme care by the health authorities on registration of medical specialties containing such active principles.

SUMMARY

We have now discovered a new process for preparing pharmaceutical compositions with an increased active substance dissolution rate which overcomes the aforesaid drawbacks and provides optimum process safety and economy.

Said process is characterised in that the active substance is co-ground or dry mixed with cyclodextrins or with a hydrophilic polymer substance which swells on contact with water and the obtained mixtures can be formulated with excipients normally used in the pharmaceutical industry and transformed into capsules or tablets of fast disgregation and dissolution or into controlled-rate release tablets.

DETAILED DESCRIPTION OF THE INVENTION

The characteristics and advantages of the process for preparing pharmaceutical compositions with an increased active substance dissolution rate according to the present invention will be more apparent from the following detailed description.

The process consists first of all of co-grinding or dry mixing the active substance with cyclodextrins or with hydrophilic polymer materials which swell on contact with water.

Normal mixing or grinding means can be used for said process, such as a pin mill, hammer mill, ball mill and/or fluid jet mills. A basic characteristic of the invention is the choice of polymer materials, which can be natural or synthetic.

The initial particle size distribution of said polymer materials is not important, and can lie within a wide range provided it falls within the limits of normal pharmaceutical use, neither do they need to have a large surface area.

A characteristic of the compositions of the invention is that when in the form of co-ground or mixed powders, transformed into tablets, they show rapid interaction with water and/or aqueous solutions to result in the development of a swelling pressure. This pressure can be measured with the apparatus described by Conte and coll, in Italian patent No. 19815 A/88 of 17/03/88.

The polymer materials used in the process of the present invention are chosen from the group consisting of crosslinked sodium carboxymethylcellulose, crosslinked polyvinylpyrrolidone, carboxymethyl starch, potassium methacrylate-divinylbenzene copolymer (ambelite IRP88), polyvinylalcohols, hydroxypropylcellulose, hydroxypropylcyclodextrin, alpha, beta, gamma cyclodextrin or derivatives and other dextran derivatives, glucans, scleroglucans and derivatives.

Synthetic or semisynthetic polymer materials of different degrees of crosslinking, different molecular weights and different properties and rates of swelling in water can also be used, such as crosslinked polyvinylpyrrolidone and crosslinked sodium carboxymethylcellulose. Natural polymer materials can also be used such as starches, modified starches, cellulose, variously substituted cellulose derivatives and formalin-casein.

The active substances usable in the process of the present invention are chosen from the group consisting of naftazone, terfenadine, carbamazepine, gliclazide, glibenclamide, bifonazole and nifedipine, diazepam, ketoprofen.

The active substance content of the composition is between 1 and 90% by weight and preferably between 10 and 75% by weight.

The mixing or co-grinding time depends on the means used for the purpose and is for example between 0.1 and 4 hours if a ball mill is used and the particle size of the co-ground product is between 0.1 and 300μ, but this dimensional distribution does not influence the active substance dissolution rate.

The described process of the invention transforms a substance poorly soluble or insoluble in water into an easily and completely soluble product in which the factor limiting the transfer is no longer the solubility of the active principle but other factors and components of the formulation.

The mixtures obtained as described ape therefore formulated with excipients normally used in the pharmaceutical industry to obtain hard gelatin capsules or tablets of fast disgregation and dissolution or controlled-rate release tablets.

In particular, by formulating the product co-ground or mixed with hydrophilic polymers able to form gels on contact with water, such as hydroxypropylcellulose, hydroxypropylmethylcellulose, sodium carboxymethylcellulose, scleroglucan, polyvinylalcohol, carboxyvinlypolymers and dextran derivatives, a reduction in the active substance transfer rate is obtained.

Some examples of the present invention are given hereinafter by way of non-limiting illustration.

EXAMPLE 1

10.0 g of naftazone (Innothera batch No. 081808) and 90.0 g of crosslinked sodium carboxymethylcellulose (AcDiSol - FMC Corporation Philadelphia USA) are placed in the jar of a ceramic ball mill (inner diameter 12 cm, capacity 1 liter) and a series of ceramic balls are added to occupy about half the available volume.

The particle size distribution of the active principle had been previously determined by usual known methods (using a Coulter counter), showing a mean diameter of 13.5 microns. The particle size distribution of the support was 20–150 microns.

Grinding is continued for 2 hours at a rotational speed of 70 rpm. A homogeneous orange coloured mixture is obtained. A dissolution test was performed on 300 mg of this mixture (equivalent to 30 mg of naftazone) to determine the dissolution rate of the active principle.

The U.S.P. 23rd Ed. apparatus in modified form was used. Specifically, a vessel was used containing 5.0 1 of $H_2O$ at 37° C. and a stirring system (paddle) rotating at 100 rpm. The stirrer blade rotated at a distance of 5 cm from the base of the vessel.

Using an automatic withdrawal system (peristaltic pump) the solution was fed to a spectrophotometer for continuous determination of the active principle concentration.

The results obtained are shown in Table I.

TABLE I

| Time (min) | Active substance dissolved (%) |
| --- | --- |
| 0 | 0 |
| 3 | 66.8 |
| 6 | 70.4 |
| 9 | 73.6 |
| 12 | 76.5 |
| 15 | 79.2 |
| 18 | 81.8 |
| 21 | 84.2 |
| 30 | 90.4 |

TABLE I-continued

| Time (min) | Active substance dissolved (%) |
| --- | --- |
| 45 | 97.8 |
| 60 | 100.0 |

EXAMPLE 2 (Comparison)

To determine whether the grinding process alone was able to influence the dissolution rate of the active substance of Example 1, a dissolution test was performed on the following, using the method indicated in Example 1:

a) on 30 mg of naftazone as such (batch No. 081808) having a particle size distribution of between 4.3 and 36.0 microns, determined with a Coulter counter;

b) on 100 g of naftazone ground for 2 hours at 70 rpm in the ball mill in the manner described in Example 1.

On termination of grinding the product was subjected to dimensional analysis (using a Coulter counter mod. T2A) and it was found that the grinding process used had not produced any marked variation in the particle size distribution, which had a mean value of 13.5 microns before grinding and a mean value of 12.8 microns after grinding.

Table II compares the results of the dissolution test.

TABLE II

| Time (min) | Test a) - Active substance dissolved % | Test b) - Active substance dissolved % |
| --- | --- | --- |
| 0 | 0 | 0 |
| 15 | 0.8 | 2.0 |
| 30 | 1.8 | 3.0 |
| 45 | 3.0 | 4.0 |
| 60 | 4.0 | 4.9 |

An examination of these data shows that grinding has irrelevant influence on the dissolution rate of the active substance.

EXAMPLE 3

Using normal methods. Flat cylindrical tablets of diameter 11.0 mm were obtained from a co-ground mixture prepared by the process described in Example 1. The press (Korsch EKO) was adjusted to produce 300 mg tablets (with an active principle content of 30 mg). The tablets obtained showed good disgregation (2–3 minutes) and excellent technical characteristics. A dissolution test was performed on these tablets using the apparatus and methods previously described for the powder mixture. The test results are given in Table III

TABLE III

| Time (min) | Active substance dissolved % |
| --- | --- |
| 0 | 0 |
| 3 | 11.1 |
| 6 | 24.0 |
| 9 | 55.0 |
| 12 | 69.4 |
| 15 | 83.4 |
| 18 | 94.0 |
| 21 | 100.0 |

EXAMPLE 4

10.0 g of naftazone (Innothera batch No. 081808) and 90.0 g of crosslinked polyvinylpyrrolidone (Polyplasdone XL - GAF Corporation, USA) are placed in the jar of a ceramic ball mill (inner diameter 12 cm, capacity 1 liter) and a series of ceramic balls are added to occupy about half the available volume.

The particle size distribution of the active principle, previously determined by usual known methods (using a Coulter counter), was 4.3–36.0 microns. The particle size distribution of the support was 20–400 microns.

Grinding is continued for 2 hours at a rotational speed of 70 rpm. A homogeneous orange coloured mixture is obtained. A dissolution test was performed on 300 mg of this mixture (equivalent to 30 mg of naftazone) to determine the dissolution rate of the active principle.

The determination was made using the apparatus and method described in Example 1.

The results obtained are shown in Table IV.

TABLE IV

| Time (min) | Active substance dissolved (%) |
| --- | --- |
| 0 | 0 |
| 3 | 44.9 |
| 6 | 68.0 |
| 9 | 78.6 |
| 12 | 84.7 |
| 15 | 88.4 |
| 18 | 91.2 |
| 21 | 93.1 |
| 30 | 96.3 |
| 45 | 99.4 |
| 60 | 100.0 |

EXAMPLE 5

Using the precise procedure described in Example 3, tablets were obtained from the powder mixture prepared as described in Example 4, these showing a disgregation time of less than 3 minutes and giving the results shown in Table V when subjected to the dissolution test.

TABLE V

| Time (min) | Active substance dissolved (%) |
| --- | --- |
| 0 | 0 |
| 3 | 48.7 |
| 6 | 79.4 |
| 9 | 89.9 |
| 12 | 94.5 |
| 15 | 97.1 |
| 18 | 98.4 |
| 21 | 99.3 |
| 30 | 100.0 |

EXAMPLE 6

To evaluate the influence of the polymer particle size on the dissolution characteristics of the active principle, a test was performed using crosslinked polyvinylpyrrolidone with a particle size distribution of 20–80 microns.

10.0 g of naftazone (Innothera batch No. 081808) and 90.0 g of crosslinked polyvinylpyrrolidone (Polyplasdone XL10 - GAF Corporation, USA) are placed in the jar of a ceramic ball mill (inner diameter 12 cm. capacity 1 liter) and a series of ceramic balls are added to occupy about half the available volume.

Grinding is continued for 2 hours at a rotational speed of 70 rpm. A homogeneous orange coloured mixture is obtained. A dissolution test was performed on 300 mg of this mixture (equivalent to 30 mg of naftazone) to determine the dissolution rate of the active principle, using the procedure described in Example 1.

Using an automatic withdrawal system (peristaltic pump) the dissolution medium was fed to a spectrophotometer for continuous determination of the active principle concentration.

The results of the dissolution test are shown in Table VI, compared with those obtained using the polymer material of coarser particle size (see Example 4).

TABLE VI

| Time (min) | Active substance dissolved (Ex. 6) % | Active substance dissolved (Ex. 4) % |
| --- | --- | --- |
| 0 | 0 | 0 |
| 3 | 62.3 | 44.9 |
| 6 | 84.6 | 68.0 |
| 9 | 90.5 | 78.6 |
| 12 | 93.2 | 84.7 |
| 15 | 94.6 | 88.4 |
| 18 | 95.4 | 91.2 |
| 21 | 96.0 | 93.1 |
| 30 | 97.2 | 96.3 |
| 45 | 98.3 | 99.4 |
| 60 | 99.3 | 100.0 |

The results show the initial polymer particle size significantly influences the release kinetics only during the initial stage (about 15 min).

EXAMPLE 7

Using the precise procedure described in Example 3, tablets were obtained from the powder mixture prepared as described in Example 6, these showing a disgregation time of less than 3 minutes and giving the results shown in Table VII when subjected to the dissolution test.

Again the results are shown compared with those obtained using the polymer material of coarser particle size (see Example 4).

TABLE VII

| Time (min) | Active substance dissolved (Ex. 7) % | Active substance dissolved (Ex. 5) % |
| --- | --- | --- |
| 0 | 0 | 0 |
| 3 | 31.9 | 48.7 |
| 6 | 66.4 | 79.4 |
| 9 | 81.0 | 89.9 |
| 12 | 88.1 | 94.5 |
| 15 | 92.1 | 97.1 |
| 18 | 94.6 | 98.4 |
| 21 | 96.5 | 99.3 |
| 30 | 99.4 | 100.0 |
| 45 | 100.0 |  |

EXAMPLE 8

10.0 g of naftazone (Innothera batch No. 081808) and 105.58 g of beta-cyclodextrin (Kleptose R - Roquette Lille France) are placed in the jar of a ceramic ball mill (inner diameter 12 cm, capacity 1 liter), these quantities being chosen to obtain a 1:2 molar ratio between the naftazone and the cyclodextrin.

A series of ceramic balls are added to occupy about half the available volume.

Grinding is continued for 2 hours at a rotational speed of 70 rpm. A homogeneous orange coloured mixture is obtained. A dissolution test was performed on this mixture (347 mg, equivalent to 30 mg of naftazone) to determine the dissolution rate of the active principle, using the apparatus and method described in Example 1. The results obtained are shown in Table VIII.

TABLE VIII

| Time (min) | Active substance dissolved (%) |
| --- | --- |
| 0 | 0 |
| 3 | 82.0 |
| 6 | 87.6 |
| 9 | 89.6 |
| 12 | 91.3 |
| 15 | 92.9 |
| 18 | 94.5 |
| 21 | 95.9 |
| 30 | 98.8 |
| 45 | 100.0 |

The results show that co-grinding naftazone with beta-cyclodextrin produces rapid dissolution of the active principle (82% in 3 minutes).

EXAMPLE 9

Using normal methods, flat cylindrical tablets of diameter 11.0 mm were obtained from a co-ground mixture prepared by the process described in Example 8. The press (Korsch EKO) was adjusted to produce 394 mg tablets (with an active principle content of 30 mg).

Their complete composition is as follows:

| | |
| --- | --- |
| Naftazone | 30 mg |
| Beta-cyclodextrin | 317 mg |
| Carboxymethyl starch | 35 mg |
| Corn starch | 10 mg |
| Magnesium stearate | 2 mg |

The flat tablets obtained showed good disgregation (4 minutes) and excellent technical characteristics. A dissolution test was also performed on these tablets using the apparatus and methods previously described.

The test results are given in Table IX

TABLE IX

| Time (min) | Active substance dissolved (%) |
| --- | --- |
| 0 | 0 |
| 3 | 89.6 |
| 6 | 97.3 |
| 9 | 98.4 |
| 12 | 98.9 |
| 15 | 99.4 |
| 18 | 99.8 |
| 21 | 100.0 |

EXAMPLE 10

Modified release forms of naftazone.

The following formulation was made up from the powder mixture obtained in example 1:

| | |
| --- | --- |
| Naftazone | 30 mg |
| Sodium carboxymethylcellulose | 270 mg |
| Hydroxypropylmethylcellulose | |

-continued

| Methocel K 4 M - Colorcon) | 75 mg |
| Magnesium stearate | 3 mg |

The relative quantities of naftazone and crosslinked sodium carboxymethylcellulose (in co-ground state) plus the remaining components of the formulation are mixed together in a powder mixer.

The mixture was pressed to obtain tablets of 12 mm diameter which were subjected to the dissolution test by the method described in Example 1.

The results, given in Table X, show that it is possible to obtain modified release of the active principle, this release slow-down being due not to the reduced solubility of the active principle but to the composition formulation.

TABLE X

| Time (min) | Active substance dissolved (%) |
|---|---|
| 0 | 0 |
| 60 | 19.7 |
| 120 | 27.3 |
| 180 | 36.9 |
| 240 | 47.8 |
| 300 | 58.7 |
| 360 | 69.1 |
| 420 | 81.1 |
| 480 | 93.3 |
| 540 | 100.0 |

EXAMPLE 11

20.0 g of terfenadine (Resfar batch R-27620-118) and 80.0 g of crosslinked sodium carboxymethylcellulose (AcD-iSol$^R$- FMC Corporation Philadelphia USA) are placed in the jar of a ceramic ball mill (inner diameter 12 cm, capacity 1 liter).

A series of ceramic balls are added to occupy about half the available volume.

Grinding is continued for 2 hours at a rotational speed of 70 rpm.

A homogeneous white coloured mixture is obtained. A dissolution test was performed on 300 mg of this mixture (equivalent to 60 mg of terfenadine) to determine the dissolution rate of the active principle.

The apparatus and method of determination were as described in Example 1, using simulated gastric fluid USPXII (5000 ml) as dissolution fluid.

The results are given in Table XI, where they are compared with those obtained by dissolution of terfenadine as such.

TABLE XI

| Time (min) | Active substance dissolved % | Terfenadine as such dissolved % |
|---|---|---|
| 0 | 0 | 0 |
| 3 | 12.2 | |
| 6 | 19.1 | |
| 0 | 33.2 | |
| 12 | 41.7 | |
| 15 | 47.5 | 10.4 |
| 21 | 60.5 | |
| 30 | 76.6 | 15.9 |
| 45 | 87.5 | 19.4 |

TABLE XI-continued

| Time (min) | Active substance dissolved % | Terfenadine as such dissolved % |
|---|---|---|
| 60 | 91.0 | 21.9 |

EXAMPLE 12

Using a Korsch EKO press fitted with flat 10 mm diameter punches, tablets weighing 300 mg (corresponding to 60 mg of terfenadine) were prepared from the powder mixture obtained by the process described in Example 11 and were subjected to the dissolution test in 5000 ml of simulated gastric fluid to USP XXII, to give the results shown in Table XII.

TABLE XII

| Time (min) | Active substance dissolved % |
|---|---|
| 0 | 0 |
| 3 | 20.9 |
| 6 | 60.5 |
| 9 | 75.9 |
| 12 | 79.0 |
| 15 | 80.0 |
| 18 | 82.0 |
| 21 | 83.0 |
| 30 | 85.0 |
| 45 | 88.0 |
| 60 | 90.0 |

EXAMPLE 13

10.0 g of terfenadine (Resfar batch R-27620-118) and 23.73 g of beta-cyclodextrin (Kleptose R - Roquette - Lille, France) (1:1 molar ratio) are placed in the jar of a ceramic ball mill (inner diameter 12 cm, capacity 1 liter). A series of ceramic balls are added to occupy about half the available volume.

Grinding is continued for 2 hours at a rotational speed of 70 rpm. A homogeneous orange coloured mixture is obtained. A dissolution test was performed on this mixture (202 mg. equivalent to 60 mg of terfenadine) to determine the dissolution rate of the active principle by means of the apparatus and method described in Example 1, using 5000 ml of simulated gastric fluid USPXXII as dissolution fluid.

The results are given in Table XIII.

TABLE XIII

| Time (min) | Active substance dissolved % |
|---|---|
| 0 | 0 |
| 3 | 17.8 |
| 6 | 32.6 |
| 9 | 41.2 |
| 12 | 49.2 |
| 15 | 55.4 |
| 18 | 60.0 |
| 21 | 63.4 |
| 30 | 69.7 |
| 45 | 73.2 |
| 60 | 74.7 |

EXAMPLE 14

Using normal technical methods, flat cylindrical tablets of diameter 10.0 mm were obtained from the powder mixture prepared by the process described in Example 13. The press (Korsch EKO) was adjusted to produce 230 mg tablets (with an active principle content of 60 mg). Their complete composition is as follows:

| | |
|---|---|
| Terfenadine | 60 mg |
| Beta-cyclodextrin (Kleptose R) | 142 mg |
| Polyvinylpyrrolidone | 20 mg |
| Corn starch | 6 mg |
| Magnesium stearate | 2 mg |

Operating in this manner, flat tablets were obtained showing excellent technical characteristics. A dissolution test was also performed on these tablets using the apparatus and methods previously described.

The test results are given in Table XIV

TABLE XIV

| Time (min) | Active substance dissolved % |
|---|---|
| 0 | 0 |
| 3 | 8.7 |
| 6 | 24.0 |
| 9 | 35.5 |
| 12 | 46.0 |
| 15 | 53.8 |
| 18 | 58.9 |
| 21 | 63.3 |
| 30 | 70.3 |
| 45 | 73.4 |
| 60 | 78.5 |

EXAMPLE 15

10.0 g of carbamazepine (Fermion - batch No. 87B18) and 40.0 g of crosslinked sodium carboxymethylcellulose (AcDiSol$^R$ - FMC Corporation Philadelphia USA) are placed in the jar of a ceramic ball mill (inner diameter 12 cm, capacity 1 liter).

A series of ceramic balls are added to occupy about half the available volume.

Grinding is continued for 2 hours at a rotational speed of 70 rpm. A homogeneous white coloured mixture is obtained. A dissolution test was performed on 200 mg of this mixture (equivalent to 40 mg of carbamazepine) to determine the dissolution rate of the active principle by means of the apparatus and method described in Example 1, using water (4000 ml at 37° C.) as dissolution fluid. The results are given in Table XV, where they are compared with those obtained by dissolution of carbamazepine as such.

TABLE XV

| Time (min) | Active substance dissolved % | Carbamazepine as such dissolved % |
|---|---|---|
| 0 | 0 | 0 |
| 3 | 27.0 | |
| 6 | 54.4 | |
| 9 | 67.8 | |
| 12 | 74.7 | |
| 15 | 79.8 | 34.0 |
| 18 | 82.9 | |
| 21 | 85.5 | |
| 30 | 92.5 | 60.1 |
| 45 | 100.0 | 83.0 |

EXAMPLE 16

10.0 g of nifedipine (Industrie Chimiche Italiane- batch No. 3671) and 90.0 g of crosslinked sodium carboxymethylcellulose (AcDiSol$^R$ - FMC Corporation Philadelphia USA) are placed in the jar of a ceramic ball mill (inner diameter 12 cm, capacity 1 liter).

A series of ceramic balls are added. Grinding is continued for 2 hours at a rotational speed of 70 rpm.

A homogeneous yellow coloured mixture is obtained. A dissolution test was performed on 100 mg of this mixture (equivalent to 10 mg of nifedipine) to determine the dissolution rate of the active principle.

The apparatus and method of determination described in Example 1 were employed, using water (4000 ml at 37° C.) as dissolution fluid. The dissolution was carried out in a dark environment because of the photosensitivity of nifedipine.

The results are given in Table XVI, where they are compared with those obtained by dissolution of nifedipine as such.

TABLE XVI

| Time (min) | Active substance dissolved % | Nifedipine as such dissolved % |
|---|---|---|
| 0 | 0 | 0 |
| 3 | 52.9 | |
| 6 | 72.2 | |
| 9 | 80.2 | |
| 12 | 84.4 | |
| 15 | 87.4 | 0.7 |
| 18 | 90.1 | |
| 21 | 92.0 | |
| 30 | 95.0 | 1.8 |
| 45 | 97.7 | 3.0 |
| 60 | 99.6 | 3.9 |

EXAMPLE 3a

Starting from co-ground Naftazone-crosslinked sodium carboxymethylcellulose 1:9 mixture prepared according to the process given in Example 1, controlled release tablets were obtained containing 30 mg active principle, with the following composition:

| | |
|---|---|
| Naftazone (Innothera Lot n. 081808) | 30 mg |
| Crosslinked sodium carboxymethylcellulose (Ac-Di-Sol) | 270 mg |
| Hydroxypropylmethylcellulose (Methocel K15M) | 50 mg |
| Magnesium stearate | 2.5 mg |

In a powder mixer the amounts of co-ground naftazone-crosslinked sodium carboxymethylcellulose are admixed with hydroxypropylmethylcellulose and magnesium stearate.

Flat tablets of φ 0 11 mm were prepared on an alternative Korsch EKO (Berlin D) press, which were submitted to a dissolution test employing the USPXXII modified apparatus described in Example 1, containing 5000 ml water, at 37° C. and with a paddle turning at 100 r.p.m.

The obtained results are reported in the following Table IIIa.

TABLE IIIa

| Time (min.) | Active substance dissolved % |
|---|---|
| 0 | 0 |
| 30 | 15.0 |
| 60 | 23.6 |

TABLE IIIa-continued

| Time (min.) | Active substance dissolved % |
|---|---|
| 120 | 34.4 |
| 240 | 56.0 |
| 360 | 82.7 |
| 480 | 99.3 |

EXAMPLE 5a

Starting from the Naftazone-cross-linked polyvinylpyrrolidone 1:9 mixture prepared according to Example 4, controlled release tablets containing 30 mg active principle were obtained having the following composition:

| | |
|---|---|
| Naftazone (Innothera, lot 081808) | 30 mg |
| Cross-linked polyvinylpyrrolidone (Polyplasdone XL) | 270 mg |
| Hydroxypropylmethylcellulose (Methocel K4M) | 75 mg |

In a powder mixer the amounts of co-ground naftazone-cross-linked polyvinylpyrrolidone are admixed with hydroxypropylmethylcellulose. Flat tablets of ϕ 11 mm are prepared on an alternative Korsch EKO press (Berlin, D) which are submitted to a dissolution test employing the USPXXII modified apparatus described in Example 1, containing 5000 ml water at 37° C., and with a paddle turning at 100 r.p.m.

The results obtained are reported in Table Va.

TABLE Va

| Time (min.) | Active substance dissolved % |
|---|---|
| 0 | 0 |
| 60 | 32.4 |
| 120 | 43.2 |
| 240 | 52.8 |
| 360 | 57.5 |
| 480 | 60.6 |
| 600 | 63.0 |
| 720 | 65.8 |
| 840 | 70.0 |
| 960 | 74.2 |
| 1080 | 76.6 |
| 1200 | 79.0 |

EXAMPLE 11a

In a glass cilinder, 20 g terfenadine (Resfar, lot n. R-27620-118) and 80 g crosslinked sodium carboxymethylcellulose (Ac-Di-Sol-FMC Corp. Philadelphia - USA) are poured.

The container is approximately half full. Stirring in a turbula mixer (Type T2A, W. A. Bachofen, Basel) is performed for 20 min. at 70 r.p.m. A homogeneous white mixture is obtained.

On 300 mg of the mixture (equal to 60 mg terfenadine) a dissolution test was performed to evaluate the solubilization speed of the active principle.

The USP XXII modified apparatus described in Example 1 was used, containing 5000 ml simulated gastric fluid USP XXII (pH 1.2) at 37° C. and a paddle stirrer at 100 r.p.m.

The results obtained are reported in the following table in comparison with the ones obtained with the corresponding co-ground product of Example 11.

TABLE XIa

| Time (min.) | Active substance dissolved % (from mixture) | Active substance dissolved % (from Ex. 11) |
|---|---|---|
| 0 | 0 | 0 |
| 3 | | 12.2 |
| 6 | 21.0 | 19.1 |
| 9 | 28.3 | 33.2 |
| 12 | 34.3 | 41.7 |
| 15 | 40.3 | 47.5 |
| 21 | 50.0 | 60.5 |
| 30 | 59.0 | 76.6 |
| 45 | 64.1 | 87.5 |
| 60 | 69.3 | 91.0 |

EXAMPLE 11b

Starting from the Terfenadine-cross-linked sodium carboxymethylcellulose (Ac-Di-Sol) 1:4 co-ground mixture prepared as reported in Example 11, controlled release tablets containing 60 mg active principle were obtained, of the following composition:

| | |
|---|---|
| Terfenadine (Resfar, lot n. R-27620-118) | 60 mg |
| Cross-linked sodium carboxy-methylcellulose (Ac-Di-Sol) | 240 mg |
| Hydroxypropylmethylcellulose (Methocel K4M) | 100 mg |

The amounts of co-ground terfenadine and cross-kinked carboxymethylcellulose are mixed in a powder mixer with the hydroxypropylmethylcellulose.

Flat tablets ϕ 10 mm are prepared on an alternative Korsch EKO (Berlin, D) press, which are submitted to a dissolution test, using the modified USP XXII apparatus described in Example 1, containing 5000 ml simulated gastric fluid USP XXII, pH 1.2 at 37° C. and paddle stirring at 100 r.p.m.

The results obtained are reported in the following Table XI b.

TABLE XI b

| Time (min.) | Dissolved active substance % |
|---|---|
| 0 | 0 |
| 30 | 35.7 |
| 60 | 53.2 |
| 120 | 73.1 |
| 240 | 89.4 |
| 360 | 94.1 |
| 480 | 97.0 |
| 600 | 98.2 |
| 720 | 98.8 |
| 840 | 100.00 |

EXAMPLE 13a

In a glass cylinder are poured:

| | |
|---|---|
| Terfenadine (Resfar, lot. n.R-27620-118) | 10.0 g |
| β-cyclodextrine (Kleptose R-Roquette, Lille, F) (1:1 molar ratio). | 23.73 g |

The container is approximately half full.

Stirring is performed in a Turbula (Tipe 12A, W. A. Bachofen, Basel-CH) mixer for 20 minutes (70 r.p.m.). A white homogeneous mixture is obtained.

On 202 mg of the mixture (equal to 60 mg terfenadine) a dissolution test was performed to evaluate the solubilization speed of the active principle.

The USP XXII modified apparatus described in Example 1 was employed, containing 5000 ml simulated gastric fluid USP XXII (pH 1.2) at 37° C. and a paddle stirrer at 100 r.p.m.

The results obtained are reported in the following table, in comparison with the corresponding co-ground product of Example 13.

TABLE XIII a

| Time (min.) | Dissolved active substance (from mixture) | Dissolved active substance (from Ex. 13) |
| --- | --- | --- |
| 0 | 0 | 0 |
| 3 | 7.8 | 17.8 |
| 6 | 15.7 | 32.6 |
| 9 | 22.6 | 41.2 |
| 12 | 27.9 | 49.2 |
| 15 | 32.6 | 55.4 |
| 18 | 36.8 | 60.0 |
| 21 | 41.2 | 63.4 |
| 30 | 51.4 | 69.7 |
| 45 | 62.0 | 73.2 |
| 60 | 67.8 | 74.7 |

EXAMPLE 13b

Starting from the co-ground Terfenadine: β-cyclodextrin (Kleptose R) 1:1 mixture prepared according to the process reported in Example 13, controlled release tablets were obtained containing 60 mg active principle, of the following composition:

| | |
| --- | --- |
| Terfenadine (Resfar, lot n. R-27620-118) | 60.0 mg |
| β-cyclodextrin (Kleptose R) | 144.36 mg |
| Hydroxypropylmethylcellulose (Methocel K4M) | 51.09 mg |

Terfenadine and β-cyclodextrin co-ground are admixed with the hydroxypropylmethylcellulose in a powder mixer.

Flat tablets are prepared of 10 mm φ on an alternative Korsch EKO (Berlin. D) press, which are then submitted to a dissolution test using the USP XXII modified apparatus described in Example 1, containing 5000 ml simulated gastric fluid USP XXII pH 1.2, at 37° C. and with paddle stirring at 100 r.p.m.

The results obtained are reported in Table XIII b:

TABLE XIII b

| Time (min.) | Dissolved active substance % |
| --- | --- |
| 0 | 0 |
| 30 | 7.9 |
| 60 | 12.1 |
| 120 | 18.1 |
| 240 | 33.9 |
| 360 | 48.4 |
| 480 | 61.2 |
| 600 | 72.7 |
| 720 | 81.7 |
| 840 | 90.2 |

TABLE XIII b-continued

| Time (min.) | Dissolved active substance % |
| --- | --- |
| 960 | 98.1 |
| 1080 | 100.00 |

EXAMPLE 15a

In a glass cylinder are poured

| | |
| --- | --- |
| Carbamazepine (Fermion, lot n. 87B18) | 10.0 g |
| Cross-linked sodium carboxymethylcellulose (Ac-Di-Sol-FMC Corp., Philadelphia-USA) | 40.0 g |

The container is approximately half full. The mixture is stirred in a Turbula (type T2A, W. A. Bachofen, Basel, CH) mixer for 20 minutes (70 r.p.m.). A white homogeneous mixture is obtained.

On 200 mg of said mixture (equal to 40 mg Carbamazepine) a dissolution test was performed, to evaluate the solubilization speed of the active principle.

The USP XXII modified apparatus described in Example 1 was employed, containing 4000 ml water at 37° C. and a paddle stirrer at 100 r.p.m. The result obtained are reported in the following table, in comparison with the ones of the corresponding co-ground product of Example 15.

TABLE XV a

| Time (min.) | Dissolved active principle (from mixture) % | Dissolved active principle (from Ex. 15) % |
| --- | --- | --- |
| 0 | 0 | 0 |
| 3 | 84.8 | 27.0 |
| 6 | 93.3 | 54.4 |
| 9 | 97.1 | 67.8 |
| 12 | 98.8 | 74.4 |
| 15 | 99.3 | 79.8 |
| 18 | 99.6 | 82.9 |
| 21 | 99.7 | 85.5 |
| 30 | 100.0 | 92.5 |
| 45 | | 100.0 |

EXAMPLE 15b

Starting from the co-ground mixture Carbamazepine-cross-linked sodium carboxymethylcellulose (Ac-Di-Sol) 1:4 prepared according to Example 15, controlled release 100 mg active principle tablets were obtained, of the following composition:

| | |
| --- | --- |
| Carbamazepine (Fermion, lot n. 87B18) | 100 mg |
| Cross-linked sodium carboxymethylcellulose (Ac-Di-Sol) | 400 mg |
| Hydroxypropylmethylcellulose (Methocel K4M) | 214 mg |

In a powder mixer the amount of co-ground carbamazepine-cross-linked carboxymethylcellulose are mixed with the hydroxypropylmethylcellulose.

Flat tablets of φ 12 mm are prepared on an alternative Korsch EKO (Berlin, D) press, which are submitted to a dissolution test using the USP XXII modified apparatus described in Example 1, containing 5000 ml water at 37° C.

and with a paddle stirrer (100 r.p.m.).

The results obtained are reported in Table XV b.

TABLE XV b

| Time (min.) | Dissolved active substance % |
|---|---|
| 0 | 0 |
| 60 | 7.4 |
| 120 | 10.7 |
| 240 | 18.9 |
| 360 | 28.5 |
| 480 | 38.9 |
| 600 | 49.8 |
| 720 | 61.0 |
| 840 | 72.1 |
| 960 | 83.4 |
| 1080 | 94.1 |
| 1200 | 99.7 |

EXAMPLE 15c

Starting from the mixture prepared in the Turbula mixer: Carbamazepine-Cross-linked sodium carboxymethylcellulose (Ac-Di-Sol) 1:4 prepared according to Example 15a, controlled release tablets containing 100 mg active principle, were prepared, having the following composition:

| | |
|---|---|
| Carbamazepine (Fermion, lot 87B18) | 100 mg |
| Cross-linked sodium carboxymethylcellulose (Ac-Di-Sol) | 400 mg |
| Hydroxypropylmethylcellulose (Methocel K4M) | 214 mg |

The previously mixed amounts of carbamazepine and cross-linked sodium carboxymethylcellulose are admixed in a powder mixer with the hydroxypropylmethylcellulose.

Flat $\phi$ 12 mm tablets were prepared on Korsch EKO alternative press, which were then submitted to a dissolution test using the modified USP XXII apparatus described in Example 1. containing 5000 ml water at 37° C. under paddle stirring at 100 r.p.m.

The obtained results are reported in the following table.

TABLE XV c

| Time (min.) | Active substance dissolved % |
|---|---|
| 0 | 0 |
| 60 | 7.8 |
| 120 | 11.2 |
| 240 | 19.0 |
| 360 | 28.1 |
| 480 | 38.2 |
| 600 | 48.9 |
| 720 | 59.8 |
| 840 | 71.1 |
| 960 | 82.6 |
| 1080 | 94.1 |
| 1200 | 100.1 |

EXAMPLE 16a

In a glass cylinder protected from light, were poured:

| | |
|---|---|
| Nifedipine (Industrie Chimiche Italiane, lot 3671) | 10.0 g |
| Cross-linked sodium carboxymethylcellulose | 90.0 g |
| (Ac-Di-Sol-FMC Corp., Philadelphia, USA) | |

The cylinder was approximately half full. Stirring was performed in a Turbula apparatus (Type T2A, W. A. Bachofen, Basel, CH) for 20 minutes (70 r.p.m.). A homogeneous light yellow mixture was obtained.

On 100 mg of said mixture (equal to 10 mg Nifedipine) a dissolution text was performed to evaluate the solubilization speed of the active principle.

The USP XXII modified apparatus described in Example 1 was used. containing 5000 ml water at 37° C. and a paddle stirrer at 100 r.p.m. The apparatus was screened from the light.

The results obtained are reported in the table in comparison with the ones of the corresponding co-ground product of Example 16.

TABLE XVI a

| Time (min.) | Dissolved active substance (from mixture) % | Dissolved active substane (from Ex. 16) % |
|---|---|---|
| 0 | 0 | 0 |
| 3 | 5.8 | 52.9 |
| 6 | 19.0 | 72.2 |
| 9 | 28.8 | 80.2 |
| 12 | 34.6 | 84.4 |
| 15 | 39.9 | 87.4 |
| 18 | 44.1 | 90.1 |
| 21 | 48.4 | 92.0 |
| 30 | 57.0 | 95.0 |
| 45 | 66.0 | 97.0 |
| 60 | 71.0 | 99.6 |

EXAMPLE 16b

Starting from the Nifedipine-cross-linked carboxymethylcellulose Ac-Di-Sol) mixture 1:9 prepared in the Turbula mixer according to Example 16a, controlled release tablets containing 30 mg active principle were prepared, having the following composition:

| | |
|---|---|
| Nifedipine (Ind. Chim. It., lot 3671) | 30 mg |
| Cross-linked sodium carboxymethylcellulose (Ac-Di-Sol) | 270 mg |
| Hydroxypropylmethylcellulose (Methocel K100M) | 130.4 mg |
| Magnesium stearate | 2.17 mg |
| Colloidal silica | 2.17 mg |

The co-ground nifedipine-cross-linked sodium carboxymethylcellulose mixture is admixed with hydroxypropylmethylcellulose, magnesium stearate and colloidal silica in a powder mixer.

Flat tablets of $\phi$ 10 mm were prepared on an alternative Korsch EKO (Berlin, D) press, which were submitted to a dissolution test in the dark using the USP XXII modified apparatus described in Example 1, containing 5000 ml water at 37° C., under paddle stirring at 100 r.p.m.

The obtained results are reported in the table.

TABLE XVI b

| Time (min.) | Dissolved active substance % |
|---|---|
| 0 | 0 |
| 120 | 10.6 |
| 240 | 17.1 |
| 360 | 24.5 |
| 480 | 32.8 |
| 600 | 42.6 |
| 720 | 53.6 |
| 840 | 65.6 |
| 960 | 77.0 |
| 1080 | 84.2 |
| 1320 | 98.2 |

EXAMPLE 17

In a glass cylinder protected from light were poured:

| | |
|---|---|
| Nifedipine (Ind. Chim. Ital., lot 3671) | 25.0 g |
| Cross-linked sodium carbossimethylcellulose (Ac-Di-Sol-FMC Corp., Philidelphia, USA) | 75.0 g |

The cylinder was approxymately half full. Stirring was performed in a Turbula mixer (Type T2A, W. A. Bachofen, Basel, CH) for 20 minutes (70 r.p.m.). A homogeneous yellow mixture was obtained.

On 400 ml of the mixture (equal to 10 mg Nifedipine) a dissolution test was performed to evaluate the solubilization speed of the active principle.

The modified USP XXII modified apparatus described in Example 1 was employed, containing 4000 ml water at 37° C., under paddle stirring at 100 r.p.m. The test was performed in the dark.

The table reports the results obtained.

TABLE XVII

| Time (min.) | Dissolved active substance % (from mixture) |
|---|---|
| 0 | 0 |
| 15 | 34.5 |
| 30 | 48.5 |
| 45 | 55.3 |
| 60 | 59.4 |
| 75 | 61.9 |
| 90 | 63.8 |
| 105 | 65.1 |
| 120 | 66.9 |

EXAMPLE 17a

Starting from the Nifedipine-cross-linked sodium carboxymethylcellulose 1:3 mixture prepared in the Turbula mixer according to Example 17, controlled release 30 mg active principle tablets were obtained, of the following composition:

| | |
|---|---|
| Nifedipine (Ind. Chim. Ital., lot 3671) | 30 mg |
| Cross-linked sodium carboxymethylcellulose (Ac-Di-Sol) | 90 mg |
| Hydroxypropylmethylcellulose (Methocel K100M) | 42 mg |
| Magnesium stearate | 0.81 mg |

The previously mixed relative amounts of nifedipine-cross-linked sodium carboxymethylcellulose are admixed with the hydroxypropylmethylcellulose and the magnesium stearate in a powder mixer.

Flat tablets of φ 8 mm are prepared on a Korsch EKO (Berlin) alternative press, which are submitted in the dark to a dissolution test using the modified USP XXIIapparatus described in Example 1, containing 5000 ml water at 37° C. under paddle stirring (100 r.p.m.). The obtained results are reported in the table.

TABLE XVII a

| Time (min.) | Dissolved active substance % |
|---|---|
| 0 | 0 |
| 60 | 12.7 |
| 120 | 20.6 |
| 240 | 34.1 |
| 360 | 48.5 |
| 480 | 64.1 |
| 600 | 77.9 |
| 720 | 87.1 |
| 840 | 92.6 |
| 960 | 94.8 |
| 1080 | 97.0 |

We claim:

1. A process for preparing a pharmaceutical tablet of terfenadine having a controlled terfenadine dissolution rate, said process consisting of co-grinding or mixing terfenadine with an agent which provides a controlled terfenadine dissolution rate and consists of cross-linked sodium carboxymethylcellulose and a hydrophilic polymer which forms a gel on contact with water, said hydrophilic polymer being selected from the group consisting of hydroxypropylmethylcellulose, hydroxylpropylcellulose, sodium carboxymethylcellulose, scleroglucan and polyvinyl alcohol, to form a mixture wherein the quantity of terfenadine used is between 1 to 90% by weight of the whole mixture, and thereafter tableting said mixture.

2. A process as defined in claim 1, wherein the particle size of the terfenadine is between 0.1 and 300 microns.

3. A process as defined in claim 1, wherein the quantity of terfenadine is between 10% and 75% by weight.

4. A process as claimed in claim 1, which consist of co-grinding a mixture of terfenadine, cross-linked sodium carboxymethylcellulose and hydroxypropylmethylcellulose, wherein terfenadine is present in an amount of 15% by weight of the whole mixture, cross-linked sodium carboxymethylcellulose is present in an amount of 60% by weight of the whole mixture and hydroxypropylmethylcellulose is present in an amount of 25% weight of the whole mixture.

\* \* \* \* \*